(12) United States Patent
Bochi

(10) Patent No.: US 9,603,676 B1
(45) Date of Patent: Mar. 28, 2017

(54) INSTRUMENT WITH LASER PROXIMITY SENSOR

(71) Applicant: Antoine Bochi, White Plains, NY (US)

(72) Inventor: Antoine Bochi, White Plains, NY (US)

(*) Notice: Subject to any disclaimer, the term of this patent is extended or adjusted under 35 U.S.C. 154(b) by 448 days.

(21) Appl. No.: 14/194,946

(22) Filed: Mar. 3, 2014

Related U.S. Application Data

(60) Provisional application No. 61/779,553, filed on Mar. 13, 2013.

(51) Int. Cl.
*A61C 3/02* (2006.01)

(52) U.S. Cl.
CPC ..................... *A61C 3/02* (2013.01)

(58) Field of Classification Search
USPC ...................... 433/131–133, 98–99
See application file for complete search history.

(56) References Cited

U.S. PATENT DOCUMENTS

| | | | |
|---|---|---|---|
| 4,308,011 A | 12/1981 | Liefke | |
| 4,593,189 A | 6/1986 | Stoub | |
| 4,745,557 A | 5/1988 | Pekar et al. | |
| 5,279,314 A * | 1/1994 | Poulos | A61C 15/047 132/322 |
| 5,668,366 A * | 9/1997 | Mauerhofer | E03D 5/10 250/221 |
| 5,933,288 A * | 8/1999 | Plesko | G02B 26/101 235/472.01 |
| 5,984,262 A * | 11/1999 | Parsons | E03C 1/057 250/221 |
| 6,031,220 A | 2/2000 | Hitz | |
| 6,878,954 B2 | 4/2005 | Butler et al. | |
| 7,253,541 B2 * | 8/2007 | Kovarik | B25F 5/00 307/117 |
| 7,488,173 B2 | 2/2009 | Bochi | |
| 7,916,282 B2 | 3/2011 | Duineveld et al. | |
| 8,204,612 B2 | 6/2012 | Feine et al. | |
| 2007/0196784 A1 * | 8/2007 | Bochi | A61B 17/1626 433/114 |
| 2011/0180686 A1 | 7/2011 | Iwai | |

\* cited by examiner

*Primary Examiner* — Jan Christopher Merene
(74) *Attorney, Agent, or Firm* — Arthur Jacob

(57) ABSTRACT

A hand held instrument and method in which a working element is to be placed by an operator into contact with a workpiece employ a laser proximity sensor arrangement adapted to sense proximity of the working element to the workpiece. A controller is responsive to the proximity sensor arrangement for activating a power source to actuate the working element in response to the working element reaching a predetermined proximity to the workpiece, as the working element is moved by the operator toward placement into contact with the workpiece. The predetermined proximity is such that the working element will reach a fully-operating condition prior to contact with the workpiece, whereby the working element will be at the fully-operating condition upon contact with the workpiece.

14 Claims, 1 Drawing Sheet

INSTRUMENT WITH LASER PROXIMITY SENSOR

Figure 1:
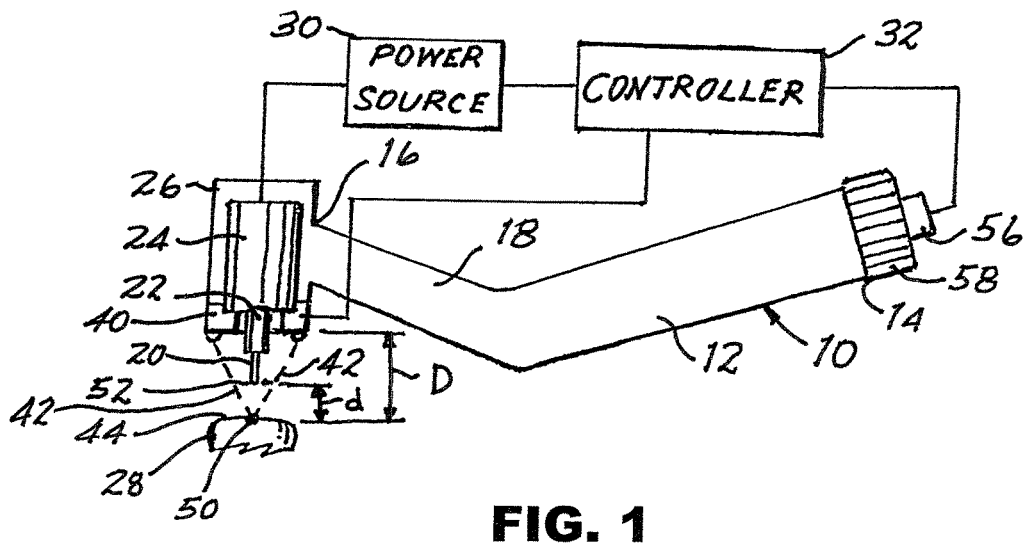

This application claims benefit of U.S. Provisional Patent Application Ser. No. 61/779,553, filed Mar. 13, 2013.

In an earlier patent, U.S. Pat. No. 7,488,173, the entire subject matter of which is incorporated herein by reference thereto, there is described a hand-held instrument and a method in which the instrument is provided with a working element, such as a drill bit, and a pressure sensor for determining the pressure between the working element and a workpiece to which the working element is applied, such that upon detecting the existence of a predetermined pressure exerted between the working element and the workpiece, the instrument will be activated to actuate the working element while that pressure continues to be exerted.

The present invention provides an improvement over the instrument described in the above earlier patent in that an instrument and method are provided wherein a proximity sensor in the form of a laser proximity sensor carried by the instrument is arranged to detect the proximity of the working element of the instrument to a workpiece so as to activate the instrument and actuate the working element before the working element makes contact with the workpiece, thereby enabling the working element to become fully actuated before reaching the workpiece. For example, where the instrument is a dental handpiece and the working element is a drill bit, known as a "burr", operated by an electric motor or a high-speed, air-driven turbine, the present invention enables the burr to reach an effective operating speed and full operating torque prior to making contact with a tooth to be treated, resulting in an increased ease of achieving accurate direction and manipulation of the burr at the site, with a decreased chance of error, while attaining increased comfort and a lessened potential for trauma on the part of the patient being treated. Upon retraction of the burr from the tooth, the instrument will be deactivated automatically when the burr reaches a predetermined distance from the tooth, thus discontinuing actuation of the burr, thereby facilitating the entire procedure, while maintaining the safety and well-being of the patient.

Accordingly, the present invention attains several objects and advantages, some of which are summarized as follows: Enables increased ease and accuracy in the manipulation and location of a working element carried by a hand-held-instrument in which the working element is actuated as it is being advanced toward a workpiece; allows a working element, such as a burr of a dental instrument, automatically to attain a full operating speed and torque before engaging a workpiece, such as a tooth of a patient, thereby promoting increased accuracy with decreased error and enhanced safety; automatically discontinues operation of a working element, such as a dental burr, upon retraction of the working element from a workpiece, such as a patient's tooth, for added safety and comfort; provides an operator with increased confidence in conducting operations in which safety and accuracy are paramount, such as in the manipulation by a dentist of a dental instrument during the application of a dental burr to a patient's tooth; renders more convenient the use of a hand-held instrument for greater accuracy with increased ease; provides a rugged instrument for reliable use over an extended service life.

The above objects and advantages, as well as further objects and advantages, are attained by the present invention which may be described briefly as a hand held instrument comprising: a handpiece having a working element to be placed by an operator into contact with a workpiece; a power source for actuating the working element between a rest condition and a fully-operating condition; a proximity sensor arrangement carried by the handpiece, the proximity sensor arrangement being adapted to sense proximity of the working element to the workpiece; and a controller for activating the power source to actuate the working element, the controller being responsive to the proximity sensor arrangement for activating the power source to actuate the working element in response to the working element reaching a predetermined proximity to the workpiece, as the working element is moved by the operator toward placement into contact with the workpiece, the predetermined proximity being such that the working element will reach the fully-operating condition prior to contact with the workpiece, whereby the working element will be at the fully-operating condition upon contact with the workpiece.

In addition, the present invention provides a method of using a handheld instrument for application to a workpiece, the method comprising: providing a handpiece having a working element to be placed by an operator into contact with a workpiece; providing a power source for actuating the working element between a rest condition and a fully-operating condition; advancing the working element toward the workpiece; sensing the proximity of the working element to the workpiece as the working element is advanced toward the workpiece; and activating the power source to actuate the working element in response to sensing that the working element has reached a predetermined proximity to the workpiece, as the working element is advanced toward placement into contact with the workpiece, the predetermined proximity being such that the working element will reach the fully-operating condition prior to contact with the workpiece, whereby the working element will be at the fully-operating condition upon contact with the workpiece.

Figure 2:
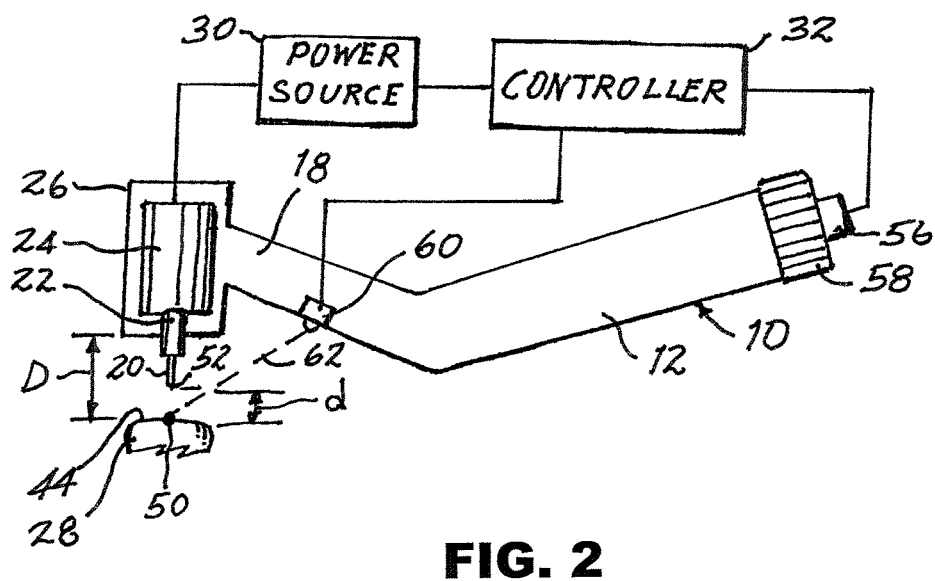

The invention will be understood more fully, while still further objects and advantages will become apparent in the following detailed description of preferred embodiments of the invention illustrated in the accompanying drawing, in which:

FIG. 1 is a somewhat diagrammatic side elevational view of a hand-held instrument constructed and being used in accordance with the present invention; and FIG. 2 is a somewhat diagrammatic side elevational view similar to FIG. 1, and showing another embodiment of the invention.

With reference to the drawing, a hand-held instrument in the form of a dental handpiece is shown, somewhat diagrammatically, at 10 and is seen to include a handle 12 extending between a proximal end 14 and a distal end 16 and having a neck 18. A working element in the form of a dental drill bit is shown in the form of a burr 20, captured in a chuck 22 operatively connected, in this instance, to an air turbine 24 held within a head 26 of the handpiece 10, with the burr 20 in position to be applied to a workpiece, here shown in the foil of a patient's tooth 28, in a now well-known manner. A power source 30 provides the air pressure that drives the air turbine 24 to rotate the burr 20, and a controller 32 serves to activate the power source 30 for actuating the air turbine 24 to operate the burr 20, and to deactivate the power source 30 for discontinuing actuation of the air turbine 24 and operation of the burr 20.

In the embodiment illustrated in FIG. 1 of the drawing, a proximity sensor in the form of a laser proximity sensor 40 is carried by the head 26 of the handpiece 10 in position to project at least one laser beam 42 toward the tooth 28. In the preferred construction, at least two laser beams 42 are projected toward the surface 44 of the tooth 28, preferably directed to converge substantially at a point 50 spaced from the tip 52 of the burr 20. When the head 26 is advanced toward the tooth 28 and reaches a distance D from the surface 44 of tooth 28, wherein the tip 52 of the burr 20 is spaced from the surface 44 of tooth 28 by a selected, predetermined distance d, the laser proximity sensor 40 will detect distance D and will signal the controller 32 to activate power source 30 to actuate the air turbine 24 for rotating the burr 20 from a rest condition toward a fully-operating condition. The distance d is selected to assure that the air turbine 24 will come up to full operation, that is, up to full speed and provide the burr 20 with full speed and torque before the tip 52 is engaged with the surface 44 of tooth 28 as the handpiece 10 is advanced by an operator toward the tooth 28. The predetermined distance d can be selected by operation of a selector 56 connected to the controller 32 and adjusted by a dial 58 placed at a location convenient to the operator. Typically, distance d will be in the range of about five to six millimeters. Thus, upon advancement of the head 26 toward the tooth 28, the burr 20 automatically will be brought from the rest condition up to speed and full torque, at the fully-operating condition, allowing the operator to manipulate handpiece 10 without requiring the performance of any supplemental operation that could distract the operator and detract from accuracy in directing the burr 20. At the same time, contact with the tooth 28 is avoided as the burr 20 is being brought up to speed, thereby avoiding the necessity of compensation for any tendency of the burr 20 to deviate from an accurate path, which deviation might otherwise be induced, causing unwanted trauma, should such contact occur before or as the burr 20 is being brought up to speed.

Upon retraction of head 26 from tooth 28, burr 20 will remain at full speed as the burr 20 is withdrawn from the tooth 28, leaving behind a clear, well-defined worked area, while avoiding potential drag on the burr 20 and concomitant forces tending to deviate the head 28, and burr 20, from an accurate, safe, trauma-free path chosen by the operator. Actuation of burr 20 will be terminated automatically when head 26 is retracted beyond distance D, thereby promoting accuracy and safety without requiring the performance of any further operation on the part of the operator.

The embodiment of the invention illustrated in FIG. 2 is similar to that shown in FIG. 1, with like component parts identified by like reference characters; however, in the present embodiment, a proximity sensor in the form of laser proximity sensor 60 is located at the neck 18 of handle 12 of handpiece 10, rather than at head 26, and provides a laser beam 62 directed toward the surface 44 of tooth 28 for detecting the distance between head 26 and point 50 on tooth 28 and, consequently, the distance d between the tip 52 of burr 20 and the surface 44 of tooth 28. As before, laser proximity sensor 60 is connected to controller 32 which, in turn, is connected to power source 30 for operating air turbine 24, and the distance d can be selected by operation of the selector 56, as adjusted by dial 58, conveniently located on handle 12 of handpiece 10.

It will be apparent that the present invention, as described above, attains all of the objects and advantages summarized above, namely: Enables increased ease and accuracy in the manipulation and location of a working element carried by a hand-held instrument in which the working element is actuated as it is being advanced toward a workpiece; allows a working element, such as a burr of a dental instrument, automatically to attain a full operating speed and torque before engaging a workpiece, such as a tooth of a patient, thereby promoting increased accuracy with decreased error and enhanced safety; automatically discontinues operation of a working element, such as a dental burr, upon retraction of the working element from a workpiece, such as a patient's tooth, for added safety and comfort; provides an operator with increased confidence in conducting operations in which safety and accuracy are paramount, such as in the manipulation by a dentist of a dental instrument during the application of a dental burr to a patient's tooth; renders more convenient the use of a hand-held instrument for greater accuracy with increased ease; provides a rugged instrument for reliable use over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A hand held instrument comprising:
   a handpiece having a working element to be placed by an operator into contact with a workpiece;
   a power source for actuating the working element between a rest condition and a fully-operating condition;
   a laser proximity sensor arrangement carried by the handpiece, the laser proximity sensor arrangement being adapted to sense proximity of the working element to the workpiece;
   a controller for activating the power source to actuate the working element, the controller being responsive to the laser proximity sensor arrangement for activating the power source to actuate the working element in response to the working element reaching a predetermined proximity to the workpiece, as the working element is moved by the operator toward placement into contact with the workpiece, the predetermined proximity being such that the working element will reach the fully-operating condition prior to contact with the workpiece, whereby the working element will be at the fully-operating condition upon contact with the workpiece; and
   the laser proximity sensor arrangement comprises at least two laser proximity sensors providing at least two corresponding laser beams converging at a point spaced from the working element, the point being located at a distance corresponding to the predetermined proximity of the working element to the workpiece.

2. The instrument of claim 1 wherein the controller is further configured for deactivating the power source in response to retraction of the working element from the workpiece, beyond the predetermined proximity from the workpiece.

3. The instrument of claim 1 wherein the distance is in the range of about five to six millimeters.

4. The instrument of claim 1 wherein the power source is a source of rotational power.

5. The instrument of claim 4 wherein the working element is a drill bit.

6. The instrument of claim 5 wherein the instrument is a dental instrument.

7. The instrument of claim 5 wherein the power source is a source of pressurized air.

8. The instrument of claim 7 wherein the instrument is a dental instrument and the working element is a turbine-driven rotary tool.

9. The instrument of claim 1 wherein the power source is a source of electrical power.

10. A method of using a handheld instrument for application to a workpiece, the method comprising:
- providing a handpiece having a working element to be placed by an operator into contact with a workpiece;
- providing a power source for actuating the working element between a rest condition and a fully-operating condition;
- advancing the working element toward the workpiece;
- providing a laser proximity sensor arrangement on the handpiece for sensing the proximity of the working element to the workpiece;
- sensing the proximity of the working element to the workpiece as the working element is advanced toward the workpiece;
- activating the power source to actuate the working element in response to sensing that the working element has reached a predetermined proximity to the workpiece, as the working element is advanced toward placement into contact with the workpiece, the predetermined proximity being such that the working element will reach the fully-operating condition prior to contact with the workpiece, whereby the working element will be at the fully-operating condition upon contact with the workpiece; and
- providing the laser proximity sensor arrangement with at least two laser proximity sensors for establishing at least two corresponding laser beams converging at a point spaced from the working element, the point being located at a distance corresponding to the predetermined proximity of the working element to the workpiece.

11. The method of claim 10 including deactivating the power source to discontinue actuation of the working element in response to retraction of the working element from the workpiece, beyond the predetermined proximity from the workpiece.

12. The method of claim 10 wherein the distance is in the range of about five to six millimeters.

13. The method of claim 10 wherein the working element is actuated to rotate in response to sensing that the working element has reached the predetermined proximity to the workpiece, as the working element is advanced toward placement into contact with the workpiece.

14. The method of claim 13 wherein the instrument is a dental instrument, the working element is a drill bit coupled to an air-driven turbine, and actuation of the working element includes directing air under pressure to the turbine.

\* \* \* \* \*